United States Patent [19]
Santos Benito et al.

[11] Patent Number: 5,514,658
[45] Date of Patent: May 7, 1996

[54] OLIGOSACCHARIDES FOR INHIBITING THE MITOSIS OF ASTROCYTES AND TUMORAL CELLS OF THE NERVOUS SYSTEM, AND METHODS FOR OBTAINING THEM

[75] Inventors: Fernando F. Santos Benito, Madrid; Manuel Nieto Sampedro, Manzanares; El Real; Alfonso Fernandez-Mayoralas; Maanuel Martin Lomas, both of Madrid, all of Spain

[73] Assignee: Consejo Superior Investigaciones Cientificas, Madrid, Spain

[21] Appl. No.: 102,131

[22] Filed: Jul. 12, 1993

[30] Foreign Application Priority Data

Nov. 13, 1991 [ES] Spain ................... 9102522

[51] Int. Cl.$^6$ .................... A61K 31/70; C07H 3/06
[52] U.S. Cl. ................ 514/25; 514/61; 536/115; 536/120; 536/124
[58] Field of Search .................. 536/115, 120, 536/124; 514/61, 25

[56] References Cited

U.S. PATENT DOCUMENTS 5,002,759  3/1991  Gaffar et al. ................ 424/49
5,118,521  6/1992  Sonoike et al. ................ 426/549

OTHER PUBLICATIONS

Santos–Benito et al. *Carbohyd. Res.* 1992, 230(1), 185–190. pub. date Jun. 12, 1992.

*Primary Examiner*—Douglas W. Robinson
*Assistant Examiner*—Kathleen Kahler Fonda
*Attorney, Agent, or Firm*—Darby & Darby

[57] ABSTRACT

A method for obtaining oligosaccharides starts with allylation of position (3') of β-lactosides followed by controlled benzylation, which leads to perbenzylated and partially benzylated compounds. The latter are glycosylated at position 3, not benzylated, with a donor of α-fucopyranosyl to yield protected trisaccharides. These and perbenzylated β-Lactosides are deallylated and, later, are glycosylated with 2-azido-2-deoxy-α-D-galactopyranosyl to yield protected tetrasaccharides and trisaccharides, respectively. The debenzylation of said products accompanied by the reduction of the azido group and simultaneous acetylation of the amino group produces intermediary products which, by O-deacetylation, leads respectively to the final tetrasaccharides and trisaccharides. The resulting oligosaccharides produce inhibition of mitosis in astrocytes and tumoral cells of the nervous system and, for this reason, can be used for controlling glial scar and for treatment of tumors of the nervous system.

25 Claims, No Drawings

OLIGOSACCHARIDES FOR INHIBITING THE MITOSIS OF ASTROCYTES AND TUMORAL CELLS OF THE NERVOUS SYSTEM, AND METHODS FOR OBTAINING THEM

This is a continuation of international application Ser. No. PCT/ES92/00074, filed Nov. 13, 1992.

FIELD OF THE INVENTION

Oligosaccharides (CO7H3) and medicinal preparations containing active organic ingredients (A61K31).

INTRODUCTION

Neuronal death or injury is always associated with an increase in the number, size and fibrous appearance of astrocytes. The transition of astrocytes from a quiescent condition to a reactive state has a great clinical signifinance because it gives way to glial scarring, a process which remains one of the main problems facing the functional recovery of the central nervous system. After a lesion, the proliferation of astrocytes precedes the axon growth and inhibits their passage through the area affected, thus making a restoration of synapsis impossible. Therefore, the repair of the central nervous system requires an outside intervention in order to modify the relative development of glial proliferation and axonal growth. The purification of the natural substances involved in the control of the glial cell division or in the synthesis of molecules similar to those natural substances is of paramount importance.

In recent studies we have demonstrated the existence in the brain of healthy rats of mitogen inhibitors for astrocytes whose levels undergo a considerable reduction following the appearance of a lesion. We have also postulated that the structural domain responsible for such an inhibition could be a carbohydrate complex related to blood groups A H or Lewis (Nieto-Sampedro, M. and Broderick, J. T. (1988). A soluble brain molecule related to epidermal growth factor receptor is a mitogen inhibitor for astrocytes, J. Neurosci. Res. 22:28–35 ). We have moreover corroborated that oligosaccharides having structures similar to the blood groups are capable of inhibiting the "in vitro" proliferation of astrocytes.

CURRENT PRIOR ART

European patent EP 0394971 (31st. Oct. 1990) claims the use of "inhibitors, containing oligosaccharides, of endothelial cell growth and angiogenesis." The patent refers to compounds which contain 6–8 saccharides in their molecule. Mention may also be made of European patent EP 0208623 (14th. Jan. 1987) under the title "The use of O-poly- and oligosaccharides for the obtention of active medicaments for the pathology of conjunctival tissues."

The compounds making the object of the present invention are new and there is, therefore, nothing published so far concerning their synthesis.

DESCRIPTION OF THE INVENTION

This patent describes a procedure for the obtention of oligosaccharides acting as mitogen inhibitors for astrocytes and tumor cells of the nervous system, probably, analogous to natural inhibitors, and investigates their inhibitory activity.

Trisaccharides of a general formula 8 and tetrasaccharides of a general formula 13 have been prepared from B-lactosides of a general formula 1. The common intermediates for the synthesis of type 8 and 13 products (compounds of general formula 2) have been the 3'-O-allyl-B-lactosides obtained from general formula 1 following a selective activation of position 3' with alkyl-tin oxides and subsequent allylation. A controlled benzylation of type 2 compounds brings about the appearance of perbenzylated compounds (3) and partially benzylated products (4). Type 3 compounds have been used for the synthesis of type 8 trisaccharides while type 4 compounds have been used for the synthesis of type 13 tetrasaccharide.

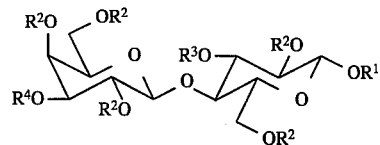

1  $R^1 = C_1$–$C_8$ n-alkyl, or $(CH_2)_7$—$CO_2Me$, or $(CH_2)_7NCBz$, or aryl 2  $R^2 = R^3 = R^4 = H$
$R^1 = C_1$–$C_8$ n-alkyl, or $(CH_2)_7$—$CO_2Me$, or $(CH_2)_7NCBz$, or aryl
$R^2 = R^3 = H$, $R^4 = $ allyl 3  $R^1 = C_1$–$C_8$ n-alkyl, or $(CH_2)_7$—$CO_2Me$, or $(CH_2)_7NCBz$, or aryl
$R^2 = R^3 = $ benzyl, $R^4 = $ allyl 4  $R^1 = C_1$–$C_8$ n-alkyl, or $(CH_2)_7$—$CO_2Me$, or $(CH_2)_7NCBz$, or aryl
$R^2 = $ benzyl, $R^3 = H$, $R^4 = $ allyl 5  $R^1 = C_1$–$C_8$ n-alkyl, or $(CH_2)_7$—$CO_2Me$, or $(CH_2)_7NCBz$, or aryl
$R^2 = R^3 = $ benzyl, $R^4 = H$ 6  $R^1 = C_1$–$C_8$ n-alkyl, or $(CH_2)_7$—$CO_2Me$, or $(CH_2)_7NCBz$, or aryl $R^2 = R^3 = $ benzyl, $R^4 = $

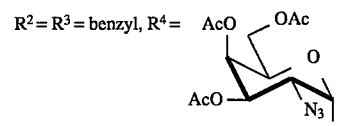

7  $R^1 = C_1$–$C_8$ n-alkyl, or $(CH_2)_7$—$CO_2Me$, or $(CH_2)_7NCBz$, or aryl $R^2 = R^3 = H$, $R^4 = $

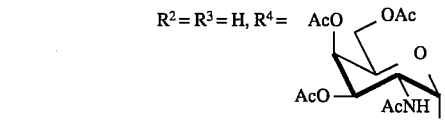

8  $R^1 = C_1$–$C_8$ n-alkyl, or $(CH_2)_7$—$CO_2Me$, or $(CH_2)_7NCBz$, or aryl $R^2 = R^3 = H$, $R^4 = $

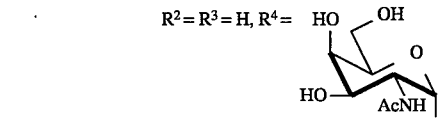

9  $R^1 = C_1-C_8$ n-alkyl, or $(CH_2)_7-CO_2Me$, or $(CH_2)_7NCBz$, or aryl

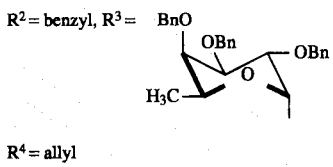

$R^4$ = allyl

10  $R^1 = C_1-C_8$ n-alkyl or $(CH_2)_7-CO_2Me$, or $(CH_2)_7NCBz$, or aryl

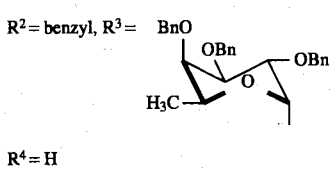

$R^4 = H$

11  $R^1 = C_1-C_8$ n-alkyl or $(CH_2)_7-CO_2Me$, or $(CH_2)_7NCBz$, or aryl, $R^2$ =benzyl

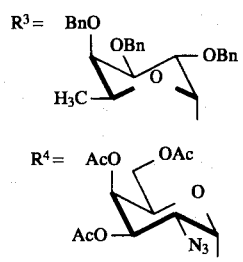

12  $R^1 = C_1-C_8$ n-alkyl or $(CH_2)_7-CO_2Me$, or $(CH_2)_7NCBz$, or aryl

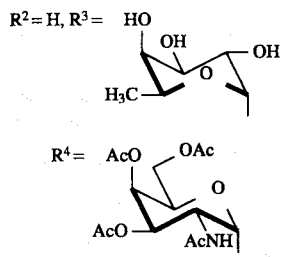

13  $R^1 = C_1-C_8$ n-alkyl, or $(CH_2)_7-CO_2Me$, or $(CH_2)_7NCBz$, aryl

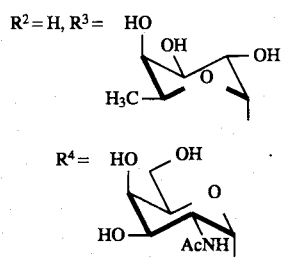

The compounds of general formula 3 have been submitted to desallylation to obtain type 5 compounds which have been glycosylated with a donor of 2-azido-desoxy-alpha-D-galactopyranosyl, giving the type 6 protected trisaccharides. The reduction of the azide group together with debenzylation and a simultaneous acetylation of the amino group have given way to type 7 intermediates which, following an O-deacetylation, led to the formation of type 8 trisaccharides.

The compounds of general formula 4 have been glycosylated with a donor of alpha-D-fucopyranosyl to give the type 9 protected trisaccharides which, through desallylation, have led to compounds of general formula 10. The type 10 compounds have been submitted to a second glycosylation reaction with a donor of 2-azide-desoxy-alpha-D-galactopyranosyl in order to give the type 11 protected tetrasaccharides. The debenzylation of the type 11 products with a concomitant reduction of the azide group and a simultaneous N-acetylation of the amine group led to the type 12 intermediates which finally gave way, by O-desacetylation, to type 13 trisaccharides.

The inhibitory activity of the synthesized oligosaccharides has been researched by analyzing its effects on the incorporation of thymidine to DNA in different cells of the nervous system during the process of cellular division. The results indicate that compounds of this type have a potential application as cellular division inhibitors, particularly for controlling the appearance of the glial scar and in the treatment of tumors in the nervous system.

The following examples illustrate the process of synthesis and show the measurements of biological activity with some of the products prepared. It must be, nevertheless, understood that the invention is not confined to the reagents and the conditions shown in the examples.

EXAMPLES

Preparation of trisaccharide 8

A mixture of methyl-B-lactoside (1 with $R^1$=Me, 17.26 g. 45.24 mmol), dibutyl-tin oxide (14.62 g., 58.75 mmol) and a type 3Å molecular sieve (58 g.) in acetonitrile (975 ml.) was heated by reflux and stirred for 14 hours. Tetrabutylammonium bromide (7.21 g., 22.38 mmol) and allyl bromide (55.2 g., 045 mol) were added thereafter, and the heating process was performed. 9 hours later, more tetrabutylammonium (2.4 g., 7.5 mmol) and allyl bromide 0.9 g., 0.15 mol) were added and the reaction was left to continue for 14 more hours. The reactive mixture was filtered and the filtrate obtained was concentrated in dry conditions. Ethyl acetate was added to the residue and the methyl 3'-allyl-B-lactoside (2 with $R^1$=Me, 7.27 g.) precipitated solid was filtered. The filtrate was concentrated and methanol was added to the resulting residue until the appearance of a crystalline solid which was filtered and discarded. The filtrate was dry-evaporated and fractionated in a silica gel column using ethyl-methanol acetate (6:1→ 3:2) as an eluent. A fraction containing 2 (5.82 g.) was obtained which was put together with the amount previously obtained.

Compound 2 (5 g., 14 mmol) was treated with benzyl-chloride (30 ml.) in the presence of potassium hydroxide (9 g.) and the mixture was heated at 100° C. for 30 minutes. It was cooled thereafter, diluted with chloroform (150 ml.) and successively washed with water. $H_2SO_4$ 1M and water. The chloroformic dissolution was dried ($Na_2SO_4$) and evaporated. The residue was passed through a silica gel column using ethyl hexane-acetate (1:0→4:1) as an eluent. Compound 3 ($R^1$= Me) (4.90 g., 41%) was first obtained and then compund 4 ($R^1$=Me) (2.92 g., 28%).

Compound 3 (5 g., 5.34 mmol) was dissolved in a mixture of ethyl-ethanol acetate-acetic acid-water (2:2:1:1, 60 ml) and heated at 80°–90° C. and stirred in the presence of a Pd 10% catalyst on active carbon (200 mg.). After 10 hours, the Pd/C was filtered, washed with chloroform, and the filtrate and the washing waters were put together and washed with an aqueous solution of NaHCO$_3$, and then with water. The organic phase was concentrated and the residue was chromatographed in a silica gel column (hexane-ethyl acetate 5:1→3:1) for the obtention of 5 (R$^1$=Me) 2.61 g., 55%

A mixture of 5 (1.5 g., 1.67 mmol), mercury cyanide (2.41 g., 9.53 mmol), mercury bromide (3.48 g., 9.65 mmol) and a type 4 Å molecular sieve in cychloromethane (85 ml) was stirred at room temperature under an argon atmosphere for 1 hour. 3,4,6-tri-o-acetyl-2-azide-deoxy-alpha-D-galactopyranosyl (0.77 g., 1.95 mmol), dissolved in dichloromethane (5 ml.), was then added, while the stirring continued. After 13 and 22 hours, more galactopyranosyl (0.85 g. each time) was added, and the reaction was left at rest for 60 hours, after which, it was filtered and the filtrate was washed successively with aqueous solutions of NaI 10%, saturated NaHCO$_3$ and water. The organic phase was dried (Na$_2$SO$_4$) and evaporated. The resulting syrup was passed through a silica gel column (hexane-ethylacetate 3:1→7:4) to give way to 6 (R$^1$=Me) (1.7 g., 87%) as a syrup $\alpha^-{}_D+61.2°$ (c=0.7 chloroform.)

Compound 6 (1.75 g., 1.45 mmol) dissolved in ethanol (100 ml), in the presence of acetic anhydride (2 ml) was hydrogenated using a palladium catalyst on active carbon (1 g.) for 4 days. The suspension was filtered on Celite and the filtrate was dry-concentrated to give a syrup that was purified on a silica gel column (chloroform-methanol 8.1). Compound 7 was obtained (R$^1$=Me) (0.75 g., 75%) m.p. 149°–151° C.) [α]$_D$+94.0° (c=0.6 methanol). This compound was dissolved in a solution of 0.1M of sodium methoxide in methanol (4 ml.) at room temperature and was left to rest for 30 minutes; it was then treated with amberlite IR - 120 (H+) until it reached a neutral point; it was also filtered and dry-concentrated to give trisaccharide 8 (R$^1$=Me) (0.54 g., 95%), as a solid. m.p. 293°– 298° C., [α]$_D$+124.5° (c=0–5 g/100 ml water).

Preparation of the tetrasaccharide 13

One mixture of 4 (R$^1$=Me) (2.94 g., 3.48 mmol) (obtained from the benzylation of 2), mercury bromide (0.4 g., 1.11 mmol), 4Å molecular sieve (5.7 g) in dichloromethane (40 ml) was stirred at room temperature for one hour. 2,3,4-tri-O-benzyl-α-L-fucopyranosyl bromide (2.4 g., 4.83 mmol), dissolved in dichloromethane (40 ml), was thereafter slowly added for 5 hours, and the stirring continued for 1 additional hour, after which, the reactive mixture was filtered over Celite, washed successively with aqueous solutions of KI 10%, saturated NaHCO$_3$ and water. The organic phase was dried (Na$_2$SO$_4$) and dry-evaporated. The syrup residue went through a silica gel column (hexane-ethyl-acetate 5:1) to obtain 9 (R$^1$=Me) (3.94 g., 84%) as a syrup. [α]$_D$–40.3° (c=0.7 chloroform).

Compound 9 (3.57 g., 2.83 mmol), dissolved in ethyl acetate (28 ml.) and ethanol 95% (140 ml.), was treated with p-toluenesulfonic acid (0.28 g.) and a palladium catalyst over activated carbon (0.52 g.) The mixture was heated at 80° C. and stirred for 1 hour and a half, after which it was filtered over Celite and evaporated following the addition of triethylamine (0.5 ml.) The resulting syrup was chromatographed on a silica gel column (hexane-ethyl-acetate 4:1) giving way to 10 (R$^1$=Me) (224 g., 65%) [α]$_D$ –40.8° (c=0.6 chloroform.)

A mixture of 10 (2.12 g., 1.73 mmol), mercury cyanide (2.1 g., 8.31 mmol), mercury bromide (3.04 g., 8.43 mmol), 4Å molecular sieve (11.4 g), in dichloromethane (76 ml) was stirred at room temperature for 1 hour, after which, a solution of 3,4,6-tri-O-acetyl-2-azide- 2-deoxy-alpha-D-galactopyranosyl bromide (2 g., 5.907 mmol), dissolved in dichoromethane (40 ml.), was added while the stirring continued. After 20, 30, 52 and 76 hours, more galactopyranosyl bromide (0.4, 0.43, 0.23 and 0.2 g., respectively) and, after 92 hours, more Hg(CN)$_2$ and HgBr$_2$ (1.05 and 1.52 g., respectively) were added. After 120 hours, the reactive mixture was filtered over Celite, and washed with aqueous solutions of KI 10%, saturated NaHCO$_3$ and water. The organic solution was dry-evaporated and the residue was passed through a silica gel column (hexane-ethyl-acetate 3:1→7.4). Compound 11 (R$^1$=Me) (2.22 g.), was then obtained, unpurified with galactopyranosyl bromide, which was applied in the following phase. This fraction (2.17 g) was dissolved in absolute ethanol (100 ml) containing acetic anhydride (1.5 ml) and was treated with hydrogen in the presence of a palladium catalyst over active carbon (0.5 g.) for 60 hours. The suspension was filtered over Celite and dry-evaporated. The residue was fractionated in a silica gel column (chloroform-methanol 6:1) giving 12 (R$^1$=Me) (0.86 g., 74%) as a solid. m.p. 162°–167° C. [α]$_D$ +28.2° (c=0.9, methanol.)

Compound 12 (0.81 g., 0.97 mmol) was treated with a solution of 0.1M sodium methoxide in methanol (150 ml.) for 30 minutes. The reactive mixture was neutralized with amberlite IR-120 (H+) and evaporated. Compound 13 was obtained (R$^1$=Me) (0.69 g., 100%), as a solid. m.p. 165°–167° C., [α]$_D$ +33.8° (c=0.4 water).

Biological Activity of Compunds 8 and 13

The mitosis inhibition brought about by the synthesized oligosaccharides was verified in vitro by measuring the incorporation of the tritiated thymidine (Nieto-Sampedro, M. (1987) Astrocyte mitogenic activity in aged normal and Alzheimer's human brain. Neurobiol. Aging. 8:249– 252) in astrocyte cultures prepared according to the method of McCarthy and de Vellis (McCarthy, K. D. and de Vellis, J. (1980). Preparation of separate astroglial and oligodendroglial cell cultures from rat cerebral tissue. J. Cell. Biol. 85:890–902 ) and in tumor cell cultures of the nervous system. Tables 1 and 2 show the concrete examples of the inhibitions produced by compounds 8 and 13 at different concentrations on astrocytes and cell lines A7 (glioma), N2A and N1E 115 (neuroblastomas.)

TABLE 1

Inhibition of the
thymidine incorporation (% with respect to control)
brought about in different cells by the compound 8 (R1 = Me)

| Conc (nM) | Astrocytes | A7 | N2A | N1E 115 |
| --- | --- | --- | --- | --- |
| 1000.0 | 89.2 | 79.5 | 72.1 | 87.3 |

TABLE 1-continued

Inhibition of the
thymidine incorporation (% with respect to control)
brought about in different cells by the compound 8 (R1 = Me)

| Conc (nM) | Astrocytes | A7 | N2A | N1E 115 |
|---|---|---|---|---|
| 500.0 | 69.6 | 55.9 | 53.2 | 73.8 |
| 250.0 | 51.3 | 41.3 | 45.7 | 54.4 |
| 125.0 | 40.3 | 19.8 | 21.6 | 21.8 |
| 62.5 | 24.8 | 7.7 | 9.6 | 11.3 |
| 31.3 | 16.0 | 0.0 | 0.0 | 0.0 |
| 15.6 | 9.9 | 0.0 | 0.0 | 0.0 |

TABLE 2

Inhibition of the
thymidine incorporation (% with respect to control)
brought about in different cells by the compound 13 (R1 = Me)

| Conc (nM) | Astrocytes | A7 | N2A | N1E 115 |
|---|---|---|---|---|
| 1000.0 | 100.0 | 90.5 | 100.0 | 100.0 |
| 500.0 | 95.4 | 79.2 | 95.1 | 96.4 |
| 250.0 | 83.1 | 69.4 | 73.8 | 64.4 |
| 125.0 | 57.8 | 36.5 | 46.3 | 40.8 |
| 62.5 | 47.9 | 23.1 | 38.2 | 22.6 |
| 31.3 | 35.2 | 18.8 | 11.2 | 8.9 |
| 15.6 | 18.7 | 9.8 | 4.1 | 0.0 |

We claim:

1. Oligosaccharides having the formula:

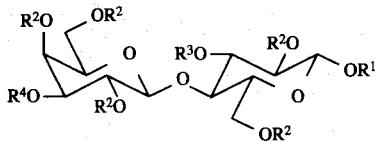

wherein $R^1 = C_1$–$C_8$ n-alkyl, $(CH_2)_7$–$CO_2CH_3$, or $(CH_2)_7NCCH_2C_6H_5$, or aryl, $R^2 = H$, $R^3 = H$, or

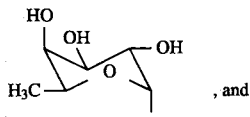, and $R^4 = $ 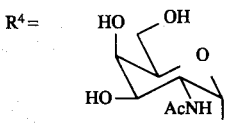.

2. A process for producing oligosaccharides according to claim 1, comprising (a) selectively allylating β-lactosides of a formula β-D-Gal-(1→4)-β-D-Glc-R wherein Gal=galactose, Glc=glucose, R=$C_8$ n-alkyl, $(CH_2)_7$ $NCCH_2C_6H_5$, or aryl at position 3';

(b) benzylating resulting 3'-O-allyl β-lactosides to form two products, one of said products being totally benzylated for use in preparation of trisaccharides having the formula alpha-D-GalNAc-(1→3)-β-D-Gal-(1→4)-β-Glc-R, wherein GalNAc=N-acetylgalactosamine, another of said products being partially benzylated, position 3 being non-benzylated, for use in preparation of tetrasaccharides having the formula alpha-D-GalNAc-(1→3)-β-D-Gal-(1→4)-(alpha-L-Fuc-(1→3))-β-D-Glc-R wherein fuc=fucose;

(c) deallylating the totally benzylated β-lactosides;

(d) stereoselectively alpha-glycosylating position 3' of the products of step (c) with 2-azide-2-deoxy-alpha-D-galactopyranosyl to form protected trisaccharides having the formula alpha-D-GalN$_3$-(1→3)-β-D-Gal (1→4)-β-D-Glc-R, wherein GalN$_3$=2-azide-2-deoxygalactose;

(e) reducing the protected trisaccharides;

(f) debenzylating, N-acetylating and O-deacetylating to give trisaccharides having the formula alpha-D-GalNAc-(1→3)-β-D-Glc-R;

(g) stereoselectively alpha-glycosylating non-benzylated β-lactosides at position 3 to form protected trisaccharides having the formula β-D-Gal-(1→4)-(alpha-L-Fuc-(1→3))-β-D-Glc-R;

(h) deallylating trisaccharides;

(i) stereoselectively alpha-glycosylating with 2-azide-2-deoxy-alpha-D-galactopyranosylto give protected tetrasaccharides having the formula alpha-D-GalN$_3$-(1→3)-β-D-Gal-( 1→4)-(alpha-L-Fuc-(1→3))-β-D-Glc-R; and (j) debenzylating, reducing and N-acetylating the products of step (g) to form tetrasaccharides having the formula alpha-D-GalN Ac-(1→3)-β-D-Gal-(1→4)-(alpha-L-Fuc-(1→3))-β-D-Glc-R.

3. A process according to claim 2 wherein in step (a), position 3' of β-lactosides is selectively allylated with an allyl halide in acetonitrile following activation with alkyl tin oxides in the presence of a molecular sieve.

4. A process according to claim 2 wherein in step (b) the 3'-O-allyl-β-lactosides are protected using a benzyl halide in the presence of potassium hydroxide at a temperature of 100° C.

5. A process according to claim 2 wherein in step (c) benzylated 3-O-allyl β-lactoside, is dissolved in a homogeneous mixture of solvents solvent, and heated at 80°–90° C. in the presence of palladium on active carbon, rhodium or iridium.

6. A process according to claim 2 wherein in step (d) alpha-glycosylation is carried out with 3,4,6-tri-O-acyl-2-azide-2-deoxy-D-galactopyranosyl trichloroacetimidate or 3,4,6-tri-O-acyl-2-azide-2-deoxy-D-galactopyranosyl halide in the presence of Lewis acid.

7. A process according to claim 2 comprising, in step (f), simultaneous debenzylation and reduction of azide group and acetylation of the resulting amine by hydrogen in the presence of a palladium catalyst on active carbon and acetic anhydride.

8. A process according to claim 2 comprising, in step (f), O-deacetylation with sodium methoxide in methanol.

9. A process according to claim 2 comprising, in step (g), selective alpha-fucosylation by 2,3-4-tri-O-benzyl fucopyranosyl trichloroacetimidate or 2,3-4-tri-O-benzylfucopyranosyl halide in the presence of a silver or a mercury catalyst or a Lewis acid.

10. A process according to claim 2 comprising, in step (h), deallylation of the trisaccharides by a rhodium, iridium or palladium catalyst on active carbon, in the presence of p-toluenesulfonic acid.

11. A process according to claim 2 comprising, in step (i), glycosylation by 3,4,6-tri-O-acyl-2-deoxy-D-galactopyranosyl trichloroacetimidate or 3,4,6-tri-O-acyl-2-deoxy-D- galacto-pyranosyl halide, in the presence of a mercury or a silver catalyst, or in the presence of a Lewis acid.

12. A process according to claim 2 comprising, in step (j), simultaneous debenzylation and reduction of the azide group and acetylation of the resulting amine by hydrogen in the presence of a palladium and acetic anhydride catalyst.

13. A process according to claim 2 further comprising O-deacetylation with sodium methoxide in methanol, in the presence of amberlite.

14. Oligosaccharides according to claim 1 wherein
$R^1$=$CH_3$,
$R^2$=H,
$R^3$=H, and $R^4$ = 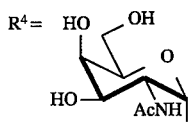

15. Oligosaccharides according to claim 1 wherein
$R^1$=$CH_3$,
$R^2$=H, $R^3$ = 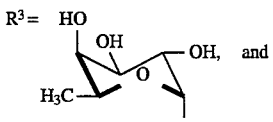 , and $R^4$ = 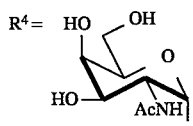

16. A process for inhibiting the growth of tumor cells comprising treating nervous system tumor cells with an oligosaccharide of claim 1.

17. A process for inhibiting the growth of tumor cells comprising treating nervous system tumor cells with an oligosaccharide of claim 14.

18. A process for inhibiting the growth of tumor cells comprising treating nervous system tumor cells with an oligosaccharide of claim 15.

19. A process for inhibiting the growth of tumor cells comprising treating glial scar with an oligosaccharide of claim 1.

20. A process for inhibiting the growth of tumor cells comprising treating glial scar with an oligosaccharide of claim 15.

21. A process for inhibiting the growth of tumor cells in an individual comprising treating nervous system tumor cells in said individual with an oligosaccharide of claim 1.

22. A process for inhibiting the growth of tumor cells in an individual comprising treating nervous system tumor cells in said individual with an oligosaccharide of claim 14.

23. A process for inhibiting the growth of tumor cells in an individual comprising treating nervous system tumor cells in said individual with an oligosaccharide of claim 15.

24. A process for inhibiting the growth of tumor cells in an individual comprising treating glial scar in said individual with an oligosaccaride of claim 1.

25. A process for inhibiting the growth of tumor cells in an individual comprising treating glial scar in said individual with an oligosaccharide of claim 15.

* * * * *

UNITED STATES PATENT AND TRADEMARK OFFICE
CERTIFICATE OF CORRECTION

PATENT NO. : 5,514,658
DATED : May 7, 1996
INVENTOR(S) : Fernando F. SANTOS BENITO et al.

It is certified that error appears in the above-indentified patent and that said Letters Patent is hereby corrected as shown below:

Title page, [75], Inventors:, change "Maanuel Martin Lomas" to --Manuel Martin Lomas--.

Signed and Sealed this

Twenty-second Day of October, 1996

Attest:

BRUCE LEHMAN

*Attesting Officer*  *Commissioner of Patents and Trademarks*